United States Patent [19]

Gossett et al.

[11] Patent Number: 5,223,503

[45] Date of Patent: Jun. 29, 1993

[54] 6-SUBSTITUTED PYRIDO[2,3-D]PYRIMIDINES AS ANTINEOPLASTIC AGENTS

[75] Inventors: Lynn S. Gossett, Indianapolis; Chuan Shih, Carmel, both of Ind.

[73] Assignee: Eli Lilly and Company, Indianapolis, Ind.

[21] Appl. No.: 832,243

[22] Filed: Feb. 7, 1992

Related U.S. Application Data

[63] Continuation-in-part of Ser. No. 692,845, Apr. 29, 1991, abandoned.

[51] Int. Cl.$^5$ .................. A61K 31/505; C07D 471/04
[52] U.S. Cl. .................................... 514/258; 544/279; 424/451; 424/456; 424/464; 424/489
[58] Field of Search ..................... 544/279; 514/258

[56] References Cited

U.S. PATENT DOCUMENTS

| | | | |
|---|---|---|---|
| 3,288,792 | 11/1966 | Hitchings et al. | 260/256.4 |
| 4,512,992 | 4/1985 | Duch et al. | 514/258 |
| 4,684,653 | 8/1987 | Taylor et al. | 514/258 |
| 4,902,796 | 2/1990 | Taylor et al. | 544/279 |

OTHER PUBLICATIONS

Hurlbert, et al., *J. Med. Chem.*, 11:711-717 (1968).
Gossett, et al., *The Fourth Chemical Congress of North America Book of Abstracts* (Am. Chem. Soc.), MEDI--0022 (1991).

*Primary Examiner*—Thurman K. Page
*Assistant Examiner*—Jyothsna Venkat
*Attorney, Agent, or Firm*—Steven A. Fontana; Leroy Whitaker

[57] ABSTRACT 2-amino-4-hydroxypyrido[2,3-d]pyrimidines, having a 6-substituted ethyl or ethenyl group, are useful antineoplastic agents.

10 Claims, No Drawings

6-SUBSTITUTED PYRIDO[2,3-D]PYRIMIDINES AS ANTINEOPLASTIC AGENTS

CROSS-REFERENCE TO RELATED APPLICATION

This application is a continuation-in-part of Application Ser. No. 07/692,845, filed Apr. 29, 1991, now abandoned.

TECHNICAL FIELD

This invention provides pyrido[2,3-d]pyrimidine derivatives which are useful as antineoplastic agents. The invention more particularly provides 2-amino-4-hydroxypyrido[2,3-d]pyrimidines having alkyl and arylalkyl substituents at the 6-position.

BACKGROUND OF THE INVENTION

Pyrido[2,3-d]pyrimidines are a class of compounds known to have a variety of biological activities. U.S. Pat. No. 3,288,792 discloses certain 2,4-diamino-6-alkyl and phenylalkyl pyrido[2,3-d]pyrimidines which are said to have antibacterial activity. U.S. Pat. No. 4,512,992 describes 2,4-diamino-6-(dialkoxybenzyl)-5-methylpyrido[2,3-d]pyrimidine as a treatment for psoriasis. Considerable interest recently has focused on a series of anticancer agents which are 2,4-diamino- and 2-amino-4-hydroxy derivatives of pyrido[2,3-d]pyrimidines having a 6-alkylbenzoyl-L-glutamic acid moiety; U.S. Pat. Nos. 4,684,653, 4,902,796, and 4,871,746. Of particular interest among this latter series is the compound lometrexol, commonly referred to as 5,10-dideazatetrahydrofolic acid or DDATHF, which has been shown to have clinical efficacy against solid tumors; Proc. Amer. Assoc. Cancer Res., 31, 1053 (1990). An object of this invention is to provide non-glutamate derivatives of DDATHF having antineoplastic activity.

SUMMARY OF THE INVENTION

The invention provides pyrido[2,3-d]pyrimidines of the formula

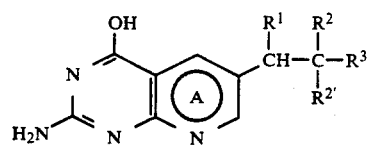

wherein
A is pyrido or tetrahydropyrido providing when A is pyrido $R^1$ together with $R^2$ is a double bond, and when A is tetrhydropyrido, $R^1$ and $R^2$ are each hydrogen;
$R^{2'}$ is hydrogen, methyl or ethyl; and
$R^3$ is phenyl; substituted phenyl wherein said substituted phenyl bears one, two or three substituents selected from a group consisting of halo, trifluoromethyl, nitro and $C_1$–$C_6$ alkyl; biphenyl; thienyl; pyridyl or naphthyl; or the pharmaceutically acceptable salts thereof.

Preferred compounds have the above formula wherein A is a tetrahydropyrido ring, $R^1$ and $R^2$ both are hydrogen and $R^3$ is phenyl substituted by one or two groups selected from halo and $C_1$–$C_6$ alkyl.

The invention also pertains to pharmaceutical formulations comprising a pyrido[2,3-d]pyrimidine of the foregoing formula together with a pharmaceutically acceptable carrier diluent or excipient therefor, and to a method of combatting neoplastic growth comprising administering a pyrido[2,3-d]pyrimidine of this invention.

DETAILED DESCRIPTION OF THE INVENTION

As noted in the foregoing formula, the pyrido[2,3-d] pyrimidines of this invention can be partially saturated, i.e., when A is tetrahydropyrido, or fully aromatic, i.e., when A is pyrido. These series of compounds have demonstrated good biological activity as antineoplastic agents.

The compounds of formula (I), and the salts thereof, have an inhibitory effect on one or more enzymes which utilize folic acid and, in particular, metabolic derivatives of folic acid, as a substrate. Neoplasms in mammals which depend upon such enzymes for growth are susceptible to treatment when an effective amount of the above compounds is administered. The term "effective amount" means that dosage of active substance to provide inhibition of such enzymes. Thus, the compounds of formula (I) are useful for treating susceptible neoplasms in mammals including, for example, choriocarcinoma, leukemia, adenocarcinoma of the female breast, epidermid cancers of the head and neck, squamous or small-cell lung cancer and various lymphosarcomas.

The compounds of the foregoing formula can exist in tautomeric equilibrium with the corresponding 3,4-dihydro-4-oxo compound, as depicted by the following scheme:

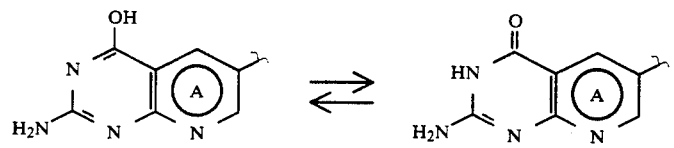

The 4-hydroxy nomenclature will be utilized throughout this specification, it being understood that the tautomeric 3,4-dihydro-4-oxo form is included.

When $R^1$ and $R^2$ together form a double bond, the resulting compounds can exist in the form of cis and trans isomers. Although both forms are within the scope of the invention and have demonstrated good biological activity, the cis form is generally preferred.

In formula (I), $R^3$ includes phenyl and substituted phenyl. The term "substituted phenyl" means a phenyl group bearing one, two or three substituents selected from halo, trifluoromethyl, nitro and $C_1$–$C_6$ alkyl.

The term "halo" refers to fluoro, chloro, bromo and iodo.

The term "$C_1$–$C_6$ alkyl" refers to the straight or branched aliphatic chains of 1–6 carbon atoms including, for example, methyl, ethyl, propyl, isopropyl, n-butyl, tert-butyl, n-hexyl and isohexyl.

The invention includes the pharmaceutically acceptable acid addition salts. Such acid addition salts include, for example, those derived from benzoic acid, hydrochloric acid, hydrobromic acid, hydroiodic acid, sulphuric acid, phosphoric acid, acetic acid, p-toluenesulphonic acid, methanesulphonic acid, maleic acid, lactic acid, citric acid, tartaric acid, succinic acid, oxalic acid, p-chlorobenzenesulphonic acid, glucuronic acid, pantothenic acid, isethionic acid and lactobionic acid.

Preferred compounds, wherein $R^3$ is a substituted phenyl group, are those wherein $R^3$ is chlorophenyl, 2,6-dichlorophenyl, 3,5-dichlorophenyl, 3-trifluoromethylphenyl, 4-isopropylphenyl, 3-fluorophenyl, 4-trifluoromethylphenyl and 3-chloro-4-trifluoromethylphenyl.

The compounds of the invention can be prepared by processes well known in the art of organic chemistry. These compounds generally are derived from 2,4-diaminopyridopyrimidines which are prepared by the following representative scheme, starting with a pyridyl-substituted triphenylphosphonium bromide derivative:

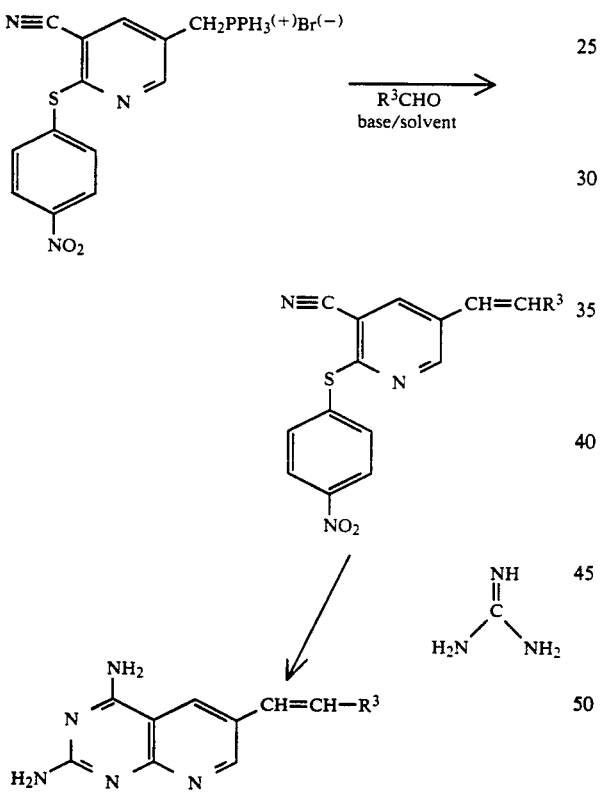

wherein $R^3$ is as defined above.

The starting compound, [(3-cyano-2-(4-nitrophenylthio)-5-pyridinyl)methyl]triphenylphosphonium bromide, is available by the method described in *J. Med. Chem.*, 28, 914, 1985. The triphenylphosphonium bromide is reacted with an arylaldehyde of the formula $R^3$CHO, wherein $R^3$ is as defined above, in the presence of a base such as triethylamine and in an organic solvent such as benzene, dichloromethane, diethyl ether, chloroform or the like. The reaction between the pyridyltriphenylphosphonium bromide and the arylaldehyde affords a 2-(4-nitrophenylthio)-3-cyano-5-arylethenylpyridine. The reaction generally is substantially complete after about one to about three hours when carried out at a temperature of about 10 to about 80° C. The 2-(4-nitrophenylthio)-3-cyano-5-arylethenylpyridine is readily isolated from the reaction mixture by simply removing the reaction solvent by evaporation, or simply filtering the product from the reaction mixture.

The 2-(4-nitrophenylthio)-3-cyano-5-arylethenylpyridine next is reacted with guanidine, generally utilized as the hydrochloride salt, in a mutual organic solvent such as ethanol, tert-butanol, xylene or the like, in the presence of a strong base such as sodium metal or the like. The reaction generally is conducted at an elevated temperature of about 50° to about 100° C., and generally is complete after about two to about three hours. While the precise amounts of reactants are not critical, the guanidine and substituted pyridine generally are utilized in about equimolar quantities, whereas the base such as sodium metal generally is used in about a one molar excess. The reaction product, a 2,4-diaminopyrido[2,3-d]pyrimidine of formula II, is readily isolated by simply cooling the reaction mixture to about 24° C. and filtering the solid precipitate. The product can be purified if desired by standard methods such as recrystallization from solvents such as alcohols or ketones, or simply washing the solid with water or an organic solvent such as diethyl ether or dichloromethane. Alternatively, the pyridopyrimidine can be reacted with a mineral acid or an organic acid to provide the corresponding acid addition salt, which generally is highly crystalline.

The following table exemplifies 2,4-diaminopyrido[2,3-d]pyrimidines which can be prepared by the foregoing process.

(II)

| $R^{2'}$ | $R^3$ |
|---|---|
| H | 2,3-dichlorophenyl |
| H | 2-bromo-4-chlorophenyl |
| $CH_3$ | 3-bromo-5-chlorophenyl |
| $CH_3$ | 3-chloro-4-trifluoromethylphenyl |
| $CH_3$ | 4-n-hexylphenyl |
| $CH_2CH_3$ | 3-thienyl |
| $CH_3$ | 1-naphthyl |
| H | 3-biphenyl |

The 2,4-diaminopyrido[2,3-d]pyrimidines of formula (II) are useful as intermediates for preparing the 2-amino-4-hydroxypyrido[2,3-d]pyrimidines of the invention, formula (III), via alkaline hydrolysis utilizing an aqueous base such as sodium hydroxide, potassium hydroxide or the like. For example, a 2,4-diaminopyrido[2,3-d]pyrimidine can be suspended in a 1N sodium hydroxide solution and heated at about 40° to about 100° C. for about 24 to about 48 hours. The product, the corresponding 2-amino-4-hydroxypyrido[2,3-d]pyrimidine, can be isolated by neutralizing the mixture by addition of an acid such as acetic acid or hydrochloric acid, and collecting the precipitated solid. If desired, acidification to pH of about 2 affords the acid addition salt. Either form of the product can be purified by conventional methods such as recrystallization or chromatography. Such crystalline forms are frequently useful for forming solutions or formulating pharmaceutical compositions. Typically, unsaturated 2-amino-4-hydroxypyrido[2,3-d]pyrimidines of the invention have the formula

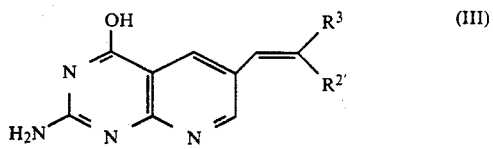

wherein $R^{2'}$ and $R^3$ are as defined above, and the following exemplary substituents are contemplated:

| $R^{2'}$ | $R^3$ |
|---|---|
| H | phenyl |
| H | 2,6-difluorophenyl |
| H | 2,3-dichlorophenyl |
| H | 3,5-dichlorophenyl |
| H | 3-bromo-4-methylphenyl |
| H | 4-isobutylphenyl |
| H | 3-thienyl |
| H | 3-pyridyl |
| $CH_3$ | 3-trifluoromethylphenyl |
| $CH_3$ | 4-n-hexylphenyl |
| $CH_2CH_3$ | 3-pyridyl |
| $CH_2CH_3$ | 2-naphthyl |
| $CH_2CH_3$ | 2-nitro-3-chlorophenyl |

The 2-amino-4-hydroxy-6-(substituted ethenyl)-pyrido[2,3-d]pyrimidines of formula (III) are converted to 2-amino-4-hydroxy-6-(substituted ethyl)-5,6,7,8-tetrahydropyrido[2,3-d]pyrimidines of formula (IV) by known hydrogenation procedures. Typically, hydrogenation reactions are carried out in a solvent such as ethanol, acetic acid or the like, in the presence of a hydrogenation catalyst such as palladium on carbon or platinum oxide. The reduced products generally are easily isolated by simply removing the hydrogenation catalyst by filtration and removing any reaction solvent by evaporation. The products can be purified, if desired, by crystallization or chromatography, and can be converted to acid addition salts such as hydrochlorides or the like. Compounds of both formula (III) and formula (IV) are active antineoplastic agents, and compounds of formula (IV) are preferred. Examples of the tetrahydropyrido[2,3-d]pyrimidines of the invention are as follows:

| $R^{2'}$ | $R^3$ |
|---|---|
| H | 3-fluorophenyl |
| H | 4-isopropylphenyl |
| H | 3,5-dichlorophenyl |
| H | 3-trifluoromethylphenyl |
| H | 4-fluorophenyl |
| H | 3-pyridyl |
| H | 2-nitrophenyl |
| $CH_3$ | 1-naphthyl |
| $CH_2CH_3$ | 3-thienyl |

Thus, 2,4-diamino-6-(substituted ethenyl)-pyrido[2,3-d]pyrimidines of formula (II) are first hydrolyzed to form compounds of formula (III), and then hydrogenated to form compounds of formula (IV). Alternatively, compounds of formula (II) are first catalytically hydrogenated to form 2,4-diamino-6-(substituted ethyl)-5,6,7,8-tetrahydropyrido[2,3-d]pyrimidines, which are then hydrolyzed to form compounds of formula (IV).

The preparation of various pyrido[2,3-d]pyrimidines provided by this invention is illustrated by the following detailed examples. The exemplification is not exhaustive of the compounds embraced by the invention, nor of the possible synthetic routes. Examples 1 through 15 are intermediate compounds whereas Examples 16-22 are final products which are useful as antineoplastic agents.

EXAMPLE 1

2,4-Diamino-6-[2-(2,6-dichlorophenyl)ethenyl]-pyrido[2,3-d]pyrimidine

To a stirred solution of 8.39 g (13.7 mM) of [(3-cyano-2-(4-nitrophenylthio)-5-pyridinyl)methyl]triphenylphosphonium bromide in 65 ml of dichloromethane were added 2.05 ml (13.7 mM) of 1,8-diazabicyclo[5.4.0]undec-7-ene (DBU). The reaction mixture was stirred at 24° C. for 30 minutes, and then diluted by dropwise addition of 2.0 g (11.4 mM) of 2,6-dichlorobenzaldehyde in 15 ml of dichloromethane. The reaction mixture was heated at reflux for two hours, cooled to 24° C., and the precipitate which formed was collected by filtration, washed with 20 ml of dichloromethane and dried to provide 3.4 g (69.7%) of a yellow solid identified as 2-(4-nitrophenylthio)-3-cyano-5-(2,6-dichlorophenyl)ethenylpyridine.

m.p.=220°-224° C. (dec.)

IR (KBr, cm$^{-1}$) 732, 773, 845, 963, 1346, 1379, 1518, 1587, 3373 and 3380

UV (ethanol) $\lambda_{max}$=433 ($\epsilon$=1805), 302 ($\epsilon$=7087), 218 ($\epsilon$=8093)

NMR (DMSOd$_6$): d 7.12 (d, 1H); 7.38 (t, 1H); 7.46 (d, 1H); 7.83 (d, 2H); 8.28 (d, 2H); 8.80 (d, 1H); 8.91 (d, 1H).

To a solution of 2.24 g (23.4 mM) of guanidine hydrochloride in 30 ml of tert.-butanol were added 0.538 g (23.4 mM) of sodium metal. The mixture was heated at 50° C. for 90 minutes, at which time 2.0 g (4.67 mM) of the 2-(4-nitrophenylthio)-3-cyano-5-(2,6-dichlorophenyl)ethenylpyridine from above were added in one portion. The mixture was heated at reflux for three hours, then cooled to 24° C., diluted by addition of 200 ml of diethyl ether, and filtered. The filter cake was washed with 30 ml of water and dried. The solid product was next washed with 20 ml of acetone and dried to afford 1.45 g (93.5% yield)

EXAMPLES 2-15

By following the general procedure of Example 1, [3-cyano-2-(4-nitrophenylthio)-5-pyridinyl)methyl]triphenylphosphonium bromide was reacted with an aryl aldehyde to produce an arylethenylpyridine intermediate, which was then reacted with guanidine to provide the following 2,4-diamino-6-substituted pyrido[2,3-d]pyrimidines:

2,4-diamino-6-[2-(thiophene)ethenyl]pyrido[2,3-d]pyrimidine m.p.=>300° C.

UV (ethanol) $\lambda_{max}$=334 ($\epsilon$=14648), 253 ($\epsilon$=20263), 217 ($\epsilon$=19838);

NMR (DMSOd$_6$): d 6.33 (broad s, 2H); 6.49 (d, 1H); 6.60 (d, 1H); 6.77 (d, 1H); 7.32-7.49 (m, 4H); 8.24 (d, 1H); 8.40 (d, 1H).

2,4-diamino-6-[2-(3,5-dichlorophenyl)ethenyl]-pyrido[2,3-d]-pyrimidine m.p. = >300° C.

UV (ethanol) $\alpha_{max}$=325 ($\epsilon$=16253), 246 ($\epsilon$=20804);

Analysis Calculated for $C_{15}H_{11}N_5Cl_2$:

Theory: C, 54.23; H, 3.34; N, 21.08; Found: C, 54.06; H, 3.47; N, 21.27.

NMR (DMSOd$_6$): d 2.42 (broad s, 2H); 6.62 (d, 1H); 6.74 (d, 1H); 7.26 (d, 1H); 7.38-7.52 (m, 3H); 7.62 (s, 1H), 8.32 (d, 1H), 8.40 (d, 1H).

2,4-diamino-6-[2-(3-fluorophenyl)ethenyl]pyrido[2,3-d]pyrimidine m.p. = >300° C.

UV (ethanol) $\lambda_{max}$=314 ($\epsilon$=13900), 245 ($\epsilon$=22800); 216 ($\epsilon$=25700).

NMR (DMSOd$_6$): d 6.38 (broad s, 2H); 6.73 (s, 2H); 7.38-7.34 (m, 4H); 8.02-8.06 (m, 2H); 8.24 (d, 1H); 8.35 (d, 1H).

2,4-diamino-6-[2-(pentafluorophenyl)ethenyl]-pyrido[2,3-d]-pyrimidine m.p. = >300° C. (dec.)

UV (ethanol) $\lambda_{max}$=338 ($\epsilon$=20700), 273 ($\epsilon$=13000).

NMR (DMSOd$_6$): d 6.51 (broad s, 2H); 7.51 (d, 1H); 7.64 (broad s, 2H); 8.10 (d, 1H), 8.81 (d, 1H), 8.85 (d, 1H).

2,4-diamino-6-[2-(biphenyl)ethenyl]pyrido[2,3-d]pyrimidine m.p. = >300° C. (dec.)

UV (ethanol) $\lambda_{max}$=317 ($\epsilon$=18100), 255 ($\epsilon$=24200).

NMR (DMSOd$_6$): d 6.25 (broad s, 2H); 6.57-6.71 (m 2H); 7.23-7.74 (m, 9H); 8.3 (d, 1H); 8.41 (d, 1H).

m.p. = >300° C. (dec.)

UV (ethanol) $\lambda_{max}$=317 ($\epsilon$=18100), 255 ($\epsilon$=24200).

NMR (DMSOd$_6$): d 6.23 (broad s, 2H); 6.57-6.71 (m 2H); 7.23-7.74 (m, 9H); 8.3 (d, 1H); 8.41 (d, 1H).

2,4-diamino-6-[2-(3-trifluoromethylphenyl)ethenyl]-pyrido[2,3-d]-pyrimidine m.p. = >293°-295° C. (dec.)

UV (ethanol) $\lambda_{max}$=312 ($\epsilon$=13900), 244 ($\epsilon$=20200), 224 ($\epsilon$=23400).

Analysis Calculated for $C_{16}H_{14}N_5F_3$

Theory: C, 58.01; H, 3.65; N, 21.14 Found: C, 58.31; H, 3.77; N, 20.92

NMR (DMSOd$_6$): d 6.36 (broad s, 2H); 6.62-6.69 (m 2H); 7.41-7.53 (m, 6H); 8.28 (d, 2H).

2,4-diamino-6-(4-isopropylphenyl)ethenyl]-pyrido[2,3-d]pyrimidine m.p. = >300° C. (dec.)

UV (ethanol) $\lambda_{max}$=319 ($\epsilon$=15072).

NMR (DMSOd$_6$): d 1.16 (s, 3H); 1.18 (s, 3H); 2.84 (m, 1H); 6.40 (broad s, 2H); 7.15 (s, 4H), 7.48 (broad s, 2H), 8.27 (d, 1H), 8.39 (d,.1H).

2,4-diamino-6-[2-(naphthyl)ethenyl]pyrido[2,3-d]pyrimidine m.p. = >300° C. (dec.)

UV (ethanol) $\lambda_{max}$=316 ($\epsilon$=17800), 291($\epsilon$=15100), 245 ($\epsilon$=23600), 218 ($\epsilon$=53300).

NMR (DMSOd$_6$): d 6.30 (broad s, 2H); 6.63 (d 1H); 6.80 (d 1H); 7.28 (d, 1H); 7.31-7.54 (m, 3H); 7.70-7.90 (m, 5H), 8.34 (d, 2H).

2,4-diamino-6-[2-(2-fluorophenyl)ethenyl]pyrido[2,3-d]pyrimidine m.p. = >300° C. (dec.)

UV (ethanol) $\lambda_{max}$=356 ($\epsilon$=9200), 311($\epsilon$=16500), 221 ($\epsilon$=25300).

NMR (DMSOd$_6$): d 6.36 (broad s, 2H); 6.58 (d, 1H); 6.68 (d, 1H); 7.02 (t, 1H); 7.12-7.30 (m, 3H), 7.41 (broad s, 2H); 8.21 (d, 1H); 8.26 (d, 1H).

2,4-diamino-6-[2-(2,6-dichlorophenyl)ethenyl]-pyrido[2,3-d]-pyrimidine.

m.p. 234°-237° C. (dec.)

IR (KBr, cm−1)=773, 845, 854, 963, 1346, 1378, 1433, 1518, 1544, 1577, 1597, 1616, 1632.

UV (ethanol) $\lambda_{max}$=443 ($\epsilon$=1114), 316($\epsilon$7931), 271 ($\epsilon$=5722), 221 ($\epsilon$=8737).

NMR (DMSOd$_6$): d 6.47 (broad s, 2H); 7.14 (t, 1H); 7.32-7.58 (m, 4H), 7.83 (d, 1H); 8.27 (d, 1H); 8.79 (d, 1H); 8.90 (d, 1H).

2,4-diamino-6-[2-(2-pyridyl)ethenyl]pyrido[2,3-d]pyrimidine m.p. = >300° C. (dec.)

UV (ethanol) $\lambda_{max}$=326 ($\epsilon$=15600), 244 ($\epsilon$=17700), 221 ($\epsilon$=20300).

NMR (DMSOd$_6$): d 6.40 (broad s, 2H); 6.66 (d, 1H); 6.76 (d, 1H); 7.20-7.29 (m 2H); 7.46 (broad s, 2H), 7.68 (d, 1H); 6.77 (d, 1H); 7.21-7.30 (m, 2H), 7.48 (broad s, 2H), 7.65-7.75 (m, 1H), 8.40 (s, 1H), 8.50 (d, 1H), 8.59 (d, 1H).

2,4-diamino-6-[2-(4-fluorophenyl)ethenyl]pyrido[2,3-d]pyrimidine m.p. = >300° C.

UV (ethanol) $\lambda_{max}$=356 ($\epsilon$=9200), 311 ($\epsilon$=16500), 221 ($\epsilon$=25300).

NMR (DMSOd$_6$): d 6.34 (broad s, 2H); 6.54 (d, 1H); 6.62 (d, 1H); 7.06 (t, 2H); 7.19-7.24 (m, 2H), 7.40 (broad s, 2H), 8.22 (d, 1H); 8.30 (d, 1H).

2,4-diamino-6-[2-(4-nitrophenyl)ethenyl]pyrido[2,3-d]pyrimidine

UV (ethanol) $\lambda_{max}$=371 ($\epsilon$=9550), 264 ($\epsilon$=5840), 254 ($\epsilon$=5710).

NMR (DMSOd$_6$): d 6.51 (broad s, 2H); 7.31 (d, 1H); 7.48 (d, 1H); 7.65 (d, 1H); 7.76-7.83 (m, 2H), 8.22 (t, 3H); 8.71 (d, 1H), 8.82 (d,. 1H)

2,4-diamino-6-[2-(4-pyridyl)ethenyl]pyrido[2,3-d]pyrimidine m.p. = 162°-166° C. (dec.)

UV (ethanol) $\lambda_{max}$=318 ($\epsilon$=6490), 248 ($\epsilon$=4160).

NMR (DMSOd$_6$): d 6.45(broad s, 2H); 6.70(d, 1H); 6.80 (d, 1H); 6.72 (d, 2H); 7.75 (broad s, 2H), 8.40 (d, 1H); 8.50 (d, 1H).

EXAMPLE 16

2-Amino-4-hydroxy-6-[2-(3,5-dichlorophenyl)ethenyl]-pyrido[2,3-d]-pyrimidine

A suspension of 0.4 g (1.2 mM) of 2,4-diamino-6-[2-(3,5-dichlorophenyl)ethenyl]pyrido[2,3-d]pyrimidine (prepared as described in Example 3), in 80 ml of 1N sodium hydroxide was heated at reflux for 24 hours. Since not all the starting material had dissolved, 10 ml of 5N sodium hydroxide and 25 ml of dioxane were added, and the mixture was heated at reflux for an additional 24 hours. The reaction mixture was cooled to 24° C., filtered, and the filtrate was diluted with 30 ml of glacial acetic acid. The precipitate which formed was collected by filtration, washed with 50 ml of water, and then with 50 ml of diethyl ether, and dried at 100° C. under vacuum to provide 160 mg of 2-amino-4-hydroxy-6-[2-(3,5-dichlorophenyl)ethenyl]pyrido-[2,3-d]pyrimidine.

m.p. = >300° C. (dec)

UV (ethanol) $\lambda_{max}$=312 ($\epsilon$=5617).

EXAMPLES 17-18

The following 4-hydroxypyrido[2,3-d]pyrimidines were prepared by alkaline hydrolysis of the corresponding 4-aminopyrido-pyrimidine according to the procedure of Example 16.

2-amino-4-hydroxy-6-[2-(3-fluorophenyl)ethenyl]-pyrido[2,3-d]-pyrimidine
100% yield
m.p.=>300° C. (dec)
UV (ethanol) $\lambda_{max}=310$ ($\epsilon=8576$), 221 ($\epsilon=11980$).

2-amino-4-hydroxy-6-[2-(4-isopropylphenyl)ethenyl]-pyrido [2,3-d]pyrimidine
yield 81%
m.p.=>300° C. (dec)
UV (ethanol) $\lambda_{max}=312$ ($\epsilon=12632$), 258 ($\epsilon=7178$).

EXAMPLE 19

2-Amino-4-hydroxy-6-[2-(3,5-dichlorophenyl)ethyl]-5,6,7,8-tetrahydropyrido[2,3-d]pyrimidine A solution of 0.165 g of 2-amino-4-hydroxy-6-[2-(3,5-dichlorophenyl)ethenyl]pyrido[2,3-d]pyridine (from Example 19 above) in 4 ml of acetic anhydride containing 9 mg of 4-N,N-dimethylaminopyridine was heated at 120° C. for thirty minutes. The reaction mixture was cooled to 24° C., filtered, and the solvent was removed by filtration under reduced pressure to provide 0.135 g (73% yield) of 2-acetamido-4-hydroxy-6-[2-(3,5-dichlorophenyl)-ethenyl]pyrido[2,3-d]pyrimidine.
m.p.=>300° C. (dec)
UV (ethanol) $\lambda_{max}=319$ ($\epsilon=11904$), 259 ($\epsilon=10264$).

A solution of 0.12 g of the foregoing compound in 20 ml of glacial acetic acid containing 0.5 g of 5% palladium on carbon was stirred under a hydrogen atmosphere at 20 psi at 24° C. for 20 hours. The mixture was filtered to remove the hydrogenation catalyst. The solvent was removed from the filtrate by evaporation under reduced pressure to provide an oil. The oil was purified by chromatography over silica gel, eluting with 8% v/v methanol in chloroform. The fractions shown by thin layer chromatography to contain the desired product were combined and concentrated to dryness to afford 25 mg of 2-acetamido-4-hydroxy-6-[2-(3,5-dichlorophenyl)ethyl]-5,6,7,8-tetrahydro[2,3-d]pyrimidine.

A 19 mg portion of the above compound was dissolved in 10 ml of methanol containing 0.42 ml of 1N sodium hydroxide. The solution was stirred at 24° C. for two hours, and then acidified to pH 5 by addition of glacial acetic acid. The mixture was extracted into ethyl acetate, and the solvent was removed by evaporation under reduced pressure to provide 14 mg (83% yield) of 2-amino-4-hydroxy-6-[2-(3,5-dichlorophenyl)ethyl]-5,6,7,8-tetrahydropyrido[2,3-d]pyrimidine.

EXAMPLES 20-22

By following the general procedures of Example 22, the following 6-(substituted ethyl)tetrahydropyridopyrimidines were prepared by catalytic hydrogenation of the corresponding 6-(substituted ethenyl)pyridopyrimidines.

2-Amino-4-hydroxy-6-[2-(3-fluorophenyl)ethyl]-5,6,7,8-tetrahydropyrido[2,3-d]pyrimidine
m.p. 255°-259° C. (dec)
Analysis Calculated for $C_{15}H_{17}N_4O$
Theory: C, 62.49; H, 5.94; N, 19.43 Found: C, 62.72; H, 6.16; N, 19.26.

2-amino-4-hydroxy-6-[2-(4-isopropylphenyl)ethyl]-5,6,7,8-tetrahydropyrido[2,3-d]pyrimidine
yield 79.5%
m.p.=>300° C. (dec)

2-amino-4-hydroxy-6-[2-(3-trifluoromethylphenyl)ethyl]-5,6,7,8-tetrahydropyrido[2,3-d]pyrimidine
m.p.=265°-271° C. (dec)
UV (ethanol) $\lambda_{max}=279$ ($\epsilon=15249$), 219 ($\epsilon=29866$).

As noted, the compounds of this invention have an effect on one or more enzymes which utilize folic acid and, in particular, metabolic derivatives of folic acid as a substrate. The resultant antineoplastic activity was established by measuring in vitro inhibitory activity ($IC_{50}$ concentrations) against whole cell human leukemia cell lines, CCRF-CEM, (Foley et al., Cancer, 18: 522 (1965)), which were grown according to the method taught by Grindey et al., (*Mol. Pharmacol.*, 16: 601 (1979)). Both references are incorporated herein by reference.

In particular, dose-response curves were generated for various compounds to determine the concentration for 50% inhibition of growth. Cluster plates were prepared in duplicate with each compound at various concentrations. Test compounds were initially dissolved in dimethylsulfoxide (DMSO) at a concentration of 4 mg/mL and further diluted with solvent to the desired concentration. Cells in 1640 media supplemented with 10% dialyzed fetal bovine serum and 16 mM HEPES buffer were added to the well at a final concentration of $3 \times 10^4$ cells/well in a total volume of 2.0 mL. After 72 hours of incubation (95% air, 5% $CO_2$), cell numbers were determined on a ZBI Coulter Counter.

The following table lists $IC_{50}$ values (mg/mL) for representative compounds of the invention.

| Compound of Example No. | $IC_{50}$ (mg/ml) |
| --- | --- |
| 16 | 6.4 |
| 17 | 14.6 |
| 19 | 4.6 |
| 20 | 2.4 |
| 21 | >20 |
| 22 | >20 |

Cytotoxicity is reversed by additions of purines such as hypoxanthine or aminoimidazole carboxamide (AICA), indicating that compounds of formula (I) inhibit either glycinamide ribonucleotide transformylase (GAR TFase), aminoimidazole carboxamide ribonucleotide transformylase, (AICAR TFase), or both. Thus, compounds of formula (I) are potent antimetabolites which are inhibitory to de novo purine synthesis.

For treatment of susceptible neoplasms in a mammal, the compounds of formula (I), alone or in combination with other therapeutic agents including other antineoplastic agents, steroids and the like, may be administered as such or they can be compounded and formulated into pharmaceutical compositions in unit dosage form for parenteral and oral administration. The preferred method of administration is oral. Such pharmaceutical compositions are prepared in a manner well known in the art and comprise at least one active compound of the above formula (I) associated with a pharmaceutically acceptable carrier.

In such a composition, the active compound and, if included, other therapeutic agents, are known as active ingredients. In making the compositions, the active ingredient(s) will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the composition can be in the form of tablets, pills, powders, lozenges, sachets, cachets, elixirs, emulsions, solutions, syrups, suspensions, soft and hard gelatin capsules, sterile injectable solutions, and sterile packaged powders. Some examples of suitable carriers, excipients, and diluents include lactose, dextrose, sucrose, sorbitol, mannitol, starches, gum acacia, calcium phosphate alginates, calcium silicate, microcrystalline cellulose, polyvinylpyrrolidone, cellulose derivatives, tragacanth, gelatin, syrup, methyl- and propylhydroxybenzoates, talc, magnesium stearate, water, and mineral oil. The formulations can additionally include lubricating agents, wetting agents, emulsifying and suspending agents, preserving agents, sweetening agents or flavoring agents. The compositions may be formulated so as to provide quick, sustained, or delayed release of the active ingredient after administration to the patient by employing procedures well known in the art. For oral administration, a compound of formula (I), optionally including other therapeutic agents, can be admixed with carriers and diluents molded into tablets or enclosed in gelatin capsules. The mixtures can alternatively be dissolved in liquids such as 10% aqueous glucose solution, isotonic saline, sterile water, or the like, and administered via parenteral routes including intramuscular, intrathecal, intravenous and intra-arterial. Such solutions will contain from about 0.5% to about 50% by weight of a compound of formula (I), ideally about 1% to about 20%.

The compositions are preferably formulated in a unit dosage form, each dosage containing from about 1 to about 500 mg and, more frequently, from about 5 to about 300 mg of the active ingredient(s). The term "unit dosage form" refers to physically discrete units suitable as unitary dosages for human subjects and other mammals, each unit containing a predetermined quantity of active material calculated to produce the desired therapeutic effect, in association with the required pharmaceutical carrier. Such compositions may contain a compound of formula (I) as an active ingredient or may contain a compound of formula (I) plus another therapeutic agent as active ingredients.

The active compounds of formula (I) are effective over a wide dosage range. For example, daily dosages will normally fall within the range of about 0.1 mg/kg to about 500 mg/kg of body weight. In the treatment of adult humans, the dosage range from about 1 mg/kg to about 300 mg/kg, in single or divided doses, is preferred. Ideal dosages range from about 10 mg/kg to about 250 mg/kg. However, it will be understood that the amount of the compound actually administered will be determined by a physician in light of the relevant circumstances including the relative severity of the neoplasm, the choice of compound or compounds to be administered, the age, weight, and response of the individual patient, and the chosen route of administration. Therefore, the above dosage ranges are not intended to limit the scope of this invention in any way. Dosage ranges for other therapeutic agents should be used according to recommendations for each agent.

Examples of typical pharmaceutical formulations contemplated by this invention include the following.

EXAMPLE 23

| Oral Suspension | |
|---|---|
| Ingredient | Amount |
| Compound of Example 16 | 300 mg |
| Sorbitol Solution (70% NF) | 40 ml |
| Sodium benzoate | 150 mg |
| Saccharin | 10 mg |
| Cherry flavor | 50 mg |
| Distilled water qs | 100 ml |

The sorbitol solution is added to 40 ml of distilled water and the pyridopyrimidine is suspended therein. The saccharin, sodium benzoate and flavoring are added, and the volume is adjusted to 100 ml with distilled water. Each ml of syrup contains 3 mg of active ingredient. The oral suspension is well suited to treating bacterial infections in children and adults.

EXAMPLE 24

| Preparation of 250 mg capsule | |
|---|---|
| Ingredient | Amount |
| Compound of Example 19 | 250 mg |
| Lactose | 150 mg |
| Corn Starch | 100 mg |
| | 500 mg |

The ingredients are blended to uniformity and encapsulation into gelatin capsules. The capsules are orally administered at the rate of about one to two each day for treating susceptible neoplasms.

We claim:

1. A compound having the formula

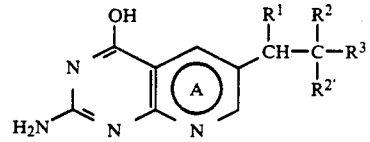

wherein:
A is pyrido or tetrahydropyrido providing when A is pyrido $R^1$ together with $R^2$ is a double bond, and when A is tetrahydropyrido $R^1$ and $R^2$ are each hydrogen;
$R^{2'}$ is hydrogen, methyl or ethyl; and
$R^3$ is phenyl; substituted phenyl, wherein said substituted phenyl is one, two or three substituents selected from a group consisting of halo, trifluoromethyl, nitro and $C_1$-$C_6$ alkyl; biphenyl; thienyl; pyridyl or naphthyl; or the pharmaceutically acceptable salt thereof.

2. A compound of claim 1 wherein A is pyrido and $R^1$ and $R^2$ together are a double bond.

3. A compound of claim 2 wherein $R^3$ is phenyl or substituted phenyl.

4. A compound of claim 3 wherein $R^3$ is 3,5-dichlorophenyl.

5. A compound of claim 2 wherein $R^3$ is naphthyl.

6. A compound of claim 1 wherein A is tetrahydropyrido and $R^1$ and $R^2$ both are hydrogen.

7. A compound of claim 6 wherein $R^3$ is phenyl or substituted phenyl.

8. A compound of claim 7 wherein $R^3$ is 3,5-dichlorophenyl.

9. A compound of claim 6 wherein $R^3$ is naphthyl.

10. A pharmaceutical composition comprising a compound of claim 1 together with a pharmaceutically acceptable excipient, carrier or diluent therefor.

* * * * *